United States Patent [19]

Kambara

[11] Patent Number: 5,541,420
[45] Date of Patent: Jul. 30, 1996

[54] MULTI-SAMPLE FRACTION COLLECTOR BY ELECTROPHORESIS

[75] Inventor: Hideki Kambara, Hachiouji, Japan

[73] Assignee: Hitachi, Ltd., Tokyo, Japan

[21] Appl. No.: 360,966

[22] Filed: Dec. 21, 1994

[30] Foreign Application Priority Data

Dec. 24, 1993 [JP] Japan .................... 5-327793

[51] Int. Cl.$^6$ .......................... G01N 27/26; G01N 33/50; B01D 57/02
[52] U.S. Cl. .......................... 204/602; 204/603; 204/605; 204/607; 204/612; 204/618; 250/573
[58] Field of Search ................ 250/573, 576, 250/221, 222.1, 461.1, 461.2; 356/344, 244, 246; 204/299 R

[56] References Cited

U.S. PATENT DOCUMENTS

| | | | |
|---|---|---|---|
| 4,624,769 | 11/1986 | Simada et al. | 204/301 |
| 4,675,095 | 6/1987 | Kambara et al. | 204/299 R |
| 4,971,677 | 11/1990 | Kambara et al. | 204/299 R |
| 5,192,412 | 3/1993 | Kambara et al. | 204/299 R |
| 5,277,780 | 1/1994 | Kambara | 204/299 R |
| 5,294,323 | 3/1994 | Togusari et al. | 204/299 R |
| 5,307,148 | 4/1994 | Kambara et al. | 356/344 |
| 5,366,608 | 11/1994 | Kambara et al. | 204/299 R |

FOREIGN PATENT DOCUMENTS

| | | |
|---|---|---|
| 2269936 | 5/1990 | Japan . |
| 3115850 | 5/1991 | Japan . |
| 6138037 | 5/1994 | Japan . |

*Primary Examiner*—Edward P. Westin
*Assistant Examiner*—John R. Lee
*Attorney, Agent, or Firm*—Antonelli, Terry, Stout & Kraus

[57] ABSTRACT

The fraction collector according to the present invention comprises a separating means composed of electrophoresis tracks to separate samples by electrophoresis, and a transferring means to transfer the separated components eluted from said electrophoresis tracks, a transferring means which comprises the capillary sample transferring tubes which are placed with their ends close to the ends of said electrophoresis tracks at the specified gap, and which transfers the separated components eluted from each electrophoresis track, a transport means to supply the buffer solution to said gap and to carry said separated component to said sample transferring tube by sheathflow of said buffer solution, a fractionating means to fractionate the separated components having moved inside said sample transfer tube, a detecting means to detect the elution of said separated component by detecting the light emitted from said separated component, and a control means to control said fractionating means based on the signal gained by said detecting means; thereby fractionating the separated components having moved inside said sample transfer tube, based on the signal gained by said detecting means.

15 Claims, 5 Drawing Sheets ated by the excitation light. The separated components after passing through the irradiated region go into the lower gel free tubes with the flow of the buffer solution.

MULTI-SAMPLE FRACTION COLLECTOR BY ELECTROPHORESIS

BACKGROUND OF THE INVENTION

The present invention relates to the multi-sample fraction collector by electrophoresis, especially to a suitable equipment used to fractionate multiple samples comprising the DNA (deoxyribonuclease), RNA (ribonuclease) or protein.

Progress in life science and biotechnology has increased the need of separating and fractionating the DNA fragments. For example, when the DNA fragments are electrophoresed using such gel as agarose polyacrylamide, they are separated according to the molecular sizes. After the gel electrophoresis, the plate is dyed with such pigment as ethidium-bromide to stain the separated DNA bands, the gel of the stained part is cut out and is immersed into the buffer solution (solvent); thus, it is possible to extract the separated DNA fragment in the buffer solution and fractionate it.

Another proposed method is to supply the solution from the perpendicular direction to the terminal portion of the gel tube used for electrophoresis, thereby eluting the separated DNA fragments into the buffer solution and fractionating it (Japanese Patent Laid-open NO. 3-115850).

SUMMARY OF THE INVENTION

The method of cutting out the gel to fractionate the DNA fragments by eluting them into the buffer solution has a disadvantage of being laborious. It also have a disadvantage that the detection sensitivity of the separated DNA is low in the conventional method of staining gel by ethidium-bromide; therefore, it is not suited for fractionation of a small amount of the DNA fragments.

Said conventional method of using the tubular electrophoresis track to elute the separated DNA fragments in the buffer solution and to fractionate them allows only one sample to be handled at one time; therefore, only a limited amount can be processed per unit time. Also it uses optical absorbance to identify the DNA fragment, resulting in a low detection sensitivity. Furthermore, when many samples are to be handled for the separation and fractionation at one time, the conventional method requires use of many electrophoresis tubes. This, in turn, requires the same number of all the equipment including the expensive detectors as that of the electrophoresis tubes, which results in a very expensive fractionation system. A long plastic tube is used for separating the separated DNA fragments, and the DNA fragments are adsorbed onto the inner wall of the tube. This makes it difficult to fractionate a small amount of components.

The objective of the present invention is to provide an innovative instrument which solves problems involved in said conventional technique, saves labor of cutting out DNA bands from the gel electrophoresis plate, permits simultaneous processing of multiple samples, and allows the separated component to be fractionated in a simple and effective manner.

The present inventor previously proposed the electrophoresis device of the invention related to Japanese Patent Laid-open NO. 6-138037. In this device, multiple capillary gel electrophoresis tubes placed between the buffer vessel with a cathode for electrophoresis and buffer vessel with an anode for electrophoresis are split into two at the mid-position, and are positioned face to face at specified gaps; the sample separated by electrophoresis is eluded into the gap and is detected. The separated component is detected by irradiating excitation light to the gap and by detecting the fluorescence emitted from fluorophore labeled DNA irradiated by the excitation light. The separated components after passing through the irradiated region go into the lower gel free tubes with the flow of the buffer solution.

The object of the invention related to Japanese Patent Laid-open NO. 6-138037 is to provide simultaneous separation of multiple samples and its effective measurement. The result of the detailed study by the present inventor has revealed that extremely simple and effective fractionation of multiple samples by addition of the appropriate fractionation function to the invented device. Namely, the object of the present invention is achieved by a fraction collecting means which is characterized by a systematic combination of the separation means comprising one or more electrophoresis tracks for separation of the sample by electrophoresis and the transfer means comprising one or more capillary sample transferring tubes positioned in the terminal end of electrophoresis track at specified gaps with the entrances face to face to one another.

Induction of the separated components eluted from the electrophoresis tracks into the capillary sample transferring tubes is carried out by supplying buffer solution to the gap between the electrophoresis tracks and sample transferring tubes, similar to the invention related to Japanese Patent Laid-open NO. 6-138037. Detection of the separated components is done by detecting fluorescence emitted from the separated components in the gap using some appropriate method, again similar to the invention related to Japanese Patent Laid-open NO. 6-138037. It should be noted, however, that the present invention provides a new means to fractionate the separated components flowing down the capillary sample transferring tubes, and the means for fractionation is controlled according to the output signal obtained by detecting the fluorescence emitted from the separated components, thereby fractionating the separated components.

The electrophoresis track for sample separation, for example, can be composed of known electrophoresis slab gel or capillary gel electrophoresis tubes, again similar to the invention related to Japanese Patent Laid-open NO. 6-138037. The number of electrophoresis tracks is not always required to be two or more. As will be described later, when using the detector which identifies the light of more than one wave length, it is possible to simultaneously separate multiple samples labeled with fluorophores having different fluorescent wavelengths by a single electrophoresis track. However, separation and fractionation of multiple samples by a single electrophoresis track have the limits as a matter of course, so use of multiple electrophoresis tracks is normally preferred. The multiple electrophoresis tracks can easily be obtained by separating electrophoresis plates using slab gel into several parts or using multiple capillary gel electrophoresis tubes. It should be noted, however, that it is necessary in this case to prepare multiple capillary sample transferring tubes corresponding to the number of the electrophoresis tracks for fractionation.

Detection of the separated components eluted from the electrophoresis tracks is carried out by detection of the fluorescence emitted from the separated component. In principle, it is possible for the detection of the separated component to use light scattering or light absorption which occurs when the separated component is exposed to light. To ensure higher detecting sensitivity, it is preferred to label the sample to be separated with fluorophore in advance, similar to the invention related to Japanese Patent Laid-open NO.

6-138037. In this case, the separated components are detected by irradiating excitation light at the opposing gap between the terminal end of electrophoresis track and capillary sample transferring tube, thereby detecting the fluorescence emitted from each separated component.

The means for fractionating separated components transferred through the capillary sample transferring tubes can be provided, for example, by sampling bottle supports provided with specified sampling bottles which are laid out so that the components can be transferred into individual sample transferring tubes. Sampling bottle supports are operated by the sampling bottle support controller according to the detection signal of the separated components eluted from the electrophoresis track, in such a way that the separated components are fractionated and put into the specified sampling bottles.

After having been separated by electrophoresis, samples (DNA fragment, for example) having smaller molecular sizes reach the terminal end of the electrophoresis track in a shorter time, and are eluted into opposing gaps from the track. The eluted separated components can be easily detected by detecting the signal light generated by the separated component (e.g. fluorescence). The buffer solution, when flowing down into the entrance of the capillary sample transferring tube by gravity, envelops the separated component eluted from the electrophoresis track, resulting in what is called "sheathflow". As a result, each separated component accompanied by the flow of the buffer solution flow smoothly and uniformly, into each sample transferring tube, without being mixed with the separated component eluted from other electrophoresis track. In order to make a stable sheathflow, it is also possible to apply appropriate pressure to the buffer solution by a pump or some other similar means.

DESCRIPTION OF THE PREFERRED EMBODIMENTS

Figure 1:
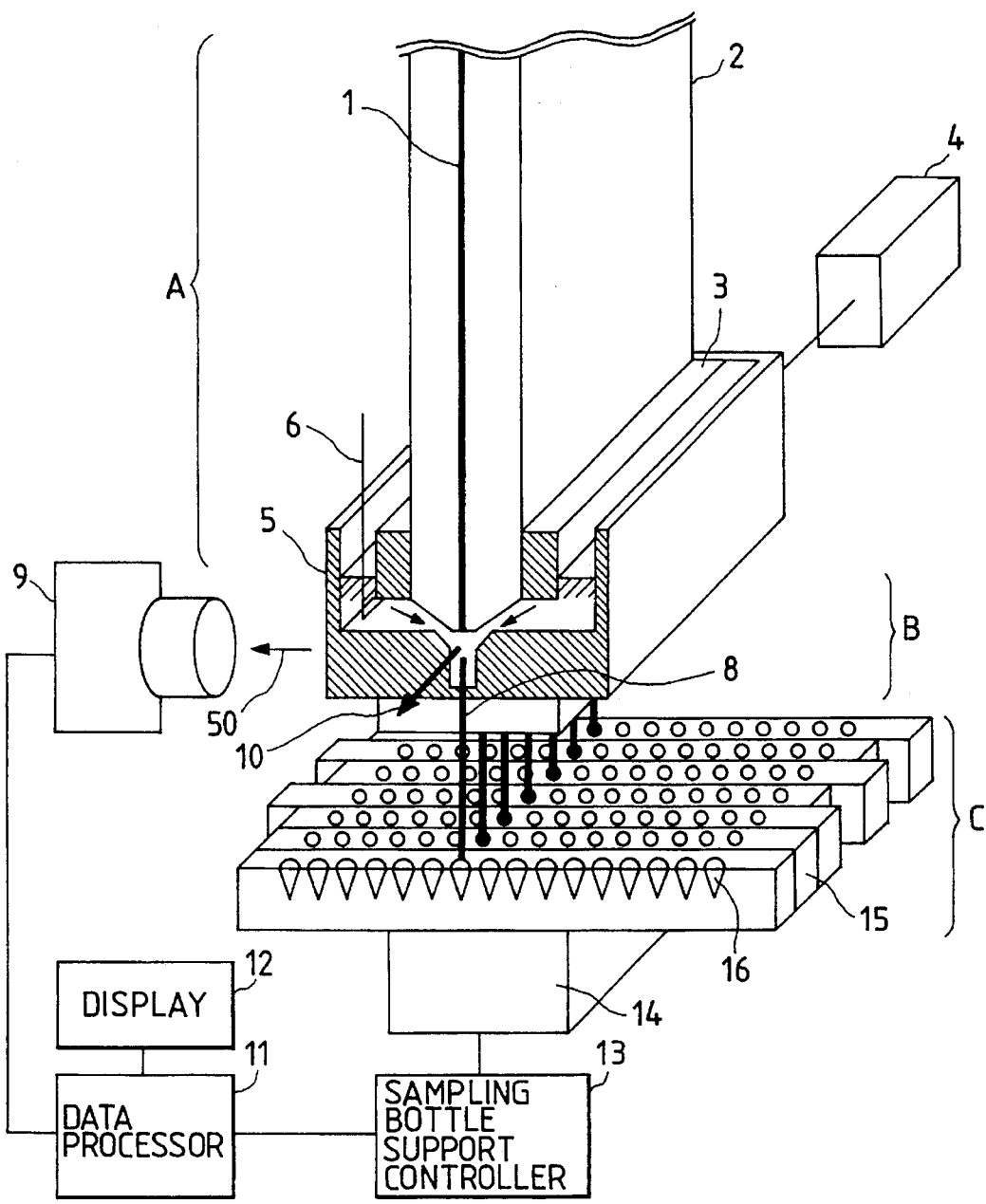
FIG. 1 is a perspective view representing the first embodiment of the fraction collector according to the present invention.

The following provides a detailed description of the fraction collector according to the present invention with reference to the two embodiments shown in the drawing:

EMBODIMENT 1

FIG. 1 shows the first embodiment of the present invention. This device comprises the separating medium A, detecting portion B and collecting portion C. The separating medium A is composed of the electrophoresis plate 1 using slab gel, in which the electrophoresis tracks are produced. Multiple samples are loaded on the top (not illustrated) at specified intervals, and samples are separated by electrophoresis with applying direct current between the cathode (not illustrated) provided on this top and anode 6 provided on the bottom. Multiple sample components are electrophoresed through different electrophoresis tracks downward in the sketch and are separated. Samples having a smaller size reach the bottom of the electrophoresis plate 1 in a shorter time, and are eluted from the bottom of the electrophoresis plate 1. Multiple electrophoresis tracks can be completely isolated by partitioning the gel electrophoresis plate 1 into several migration tracks using the isolation wall (this makes several grooves as the migration tracks). Polyacrylamide gel having a concentration of 5 to 20 percent or agarose gel having a concentration of 0.5 to 3 percent is often used as separation gel.

Detecting portion B is composed of buffer vessel 5, excitation light source 4 and two-dimensional detector 9. Buffer vessel 5 has a slender structure extending along the overall length of gel electrophoresis plate 1 in the horizontal direction, and a sufficient amount of buffer solution to immerse the entire bottom of the gel electrophoresis plate 1 is supplied. The irradiating angle of excitation light 10 is adjusted so that all separated components eluted from the multiple electrophoresis tracks will be exposed to it.

When samples labeled with fluorophore are used, the separated components eluted from the gel electrophoresis plate 1 receive excitation light 10 from light source 4 to emit fluorescence 50. A high sensitivity detection of separated components is carried out by detecting the emitted fluorescence using the two-dimensional detector 9. To minimize the influence of the background signal from other substances (gel, etc.) than separated components, the optical axis of excitation light 10 is positioned in advance for the separated components immediately after having been eluted from the gel electrophoresis plate 1 to be exposed to excitation light 10.

The collecting portion C comprises the multiple capillary sample transferring tubes 8, a corresponding number of sampling bottle supports 15, transfer devices 14 for sampling bottle supports and controllers 13 of the transfer device 14. The data processor 11 processes the output signal of two-dimensional detector 9, and transmits to controller 13. Sample transferring tubes 8 can transfer the separated components eluted from each electrophoresis track, to sampling bottle support 15. They are arranged in one row in conformity to the shape of the bottom of electrophoresis plate 1, and are connected to the bottom of buffer vessel 5, with the tops (entrance) held together.

The buffer solution in buffer vessel 5 flows down spontaneously toward the entrance of sample transferring tube 8, and carries separated components eluted from electrophoresis track of gel electrophoresis plate 1 into the sample transferring tube 8. To provide smooth transfer of the separated components with buffer solution into the sample transferring tubes and to ensure separated components to be exposed to excitation light, an opposing gap of about 1 mm is provided between the bottom (terminal of the electrophoresis track) of the gel electrophoresis plate 1 and the top (entrance) of the sample transferring tube 8.

Multiple sampling bottle supports 15 are orderly arranged in opposition to the bottom of sample transferring tube 8 (exit) so that the separated components flowing down in the sample transferring tube 8 can be fractionated together with buffer solution for each electrophoresis track. The present embodiment uses sampling bottle supports 15 formed in straight lines by arranging the wells working as sampling bottles 16 having a diameter of 4 mm at intervals of 5 mm in rectangular blocks. Instead of forming wells, it is possible to arrange the specified number of the plastic bottles available in the market.

The transfer device 14 of the sampling bottle support 15 is controlled by the sampling bottle support controller 13 which is operated according to the control data preset in data processor 11. The average migration time required for the separated component eluted from electrophoresis track of gel electrophoresis plate 1 to arrive at the terminal of the sample transferring tube 8 is set as the control data. This average migration time can be calculated from the time determined by the flow rate of the buffer solution flowing through the sample transferring tube 8 and the length of the sample transferring tube 8. Normally, this average migration time is calculated by making the marker flow prior to fractionation, thereby measuring the time required for the maker to pass by the sample transferring tube 8. The present embodiment also used the method of obtaining the average migration time by making the maker flow, where the result was set as control data. The sampling bottle support controller 13 controls the transfer device 14 based on this control data. The transfer device 14 the controlled by sampling bottle support controller 13 moves the sampling bottle support 15 in conformity to separated component elution timing. Namely, after the detection signal of the separated component eluted from the electrophoresis track has been detected by the two-dimensional detector 9, sampling bottle support 15 is moved by the transfer device 14 controlled by sampling bottle support controller 13 based on the control data (average migration time). Then the specified sampling bottle 16 is moved in conformity to the timing when the separated component is eluted from electrophoresis track, and the separated component is fractionated and is collected into the specified sampling bottle 16. This ensures fractionation of a great number of DNA fragments with extreme efficiency. It should be noted that the sampling bottle support 15 can be moved intermittently at specified time intervals.

The fractionated sample is prepared by mixing the buffer solution with the DNA fragment cut off by 6-base recognition enzyme ECoRI, a restriction enzyme which recognizes 6 bases and cuts them off. For labeling the DNA fragment, the oligomer labeled with sulforhodamine 101 (having a fluorescent wavelength of 620 nm) was connected to the cutting site of the DNA fragment by ligation reaction. It is also possible to label the DNA fragment with fluorophore by linking the fluorophore labeled nucleic acid to the cutting site of the DNA, using the polymerase reaction by the DNA polymerase. Excitation light from the light source using the He-Ne laser (fluorescent waveform of 594 nm) is used for detection of the DNA fragments eluted from the gel electrophoresis plate. In addition, it is also possible to separate and fractionate various sizes of the single stranded DNAs obtained by complementary strand extension reaction using the fluorophore labeled deoxynucleotide and the single stranded template DNA obtained by decomposing the double stranded sample DNA.

In the present embodiment, free fall is used to sample the separated components for the sampling bottle 16. To facilitate separation of the components from the capillary sample transferring tube 8, supersonic oscillation is applied to the terminum of the sample transferring tube 8 or the ink jet function is mounted on the terminum of the sample transferring tube 8. This will permit a small amount of separated components to be collected with higher efficiency. Use of smallest possible sample transferring tube 8 is preferred to prevent the separated component from being adsorbed on the inner wall of the bottle. According to the present embodiment, the equipment configuration is designed by laying out the gel electrophoresis plate 1 and capillary sample transferring tube 8 in the vertical direction. It is also possible to lay out the gel electrophoresis plate 1 in the horizontal direction and the sample transferring tube 8 in the vertical direction.

EMBODIMENT 2

Figure 2:
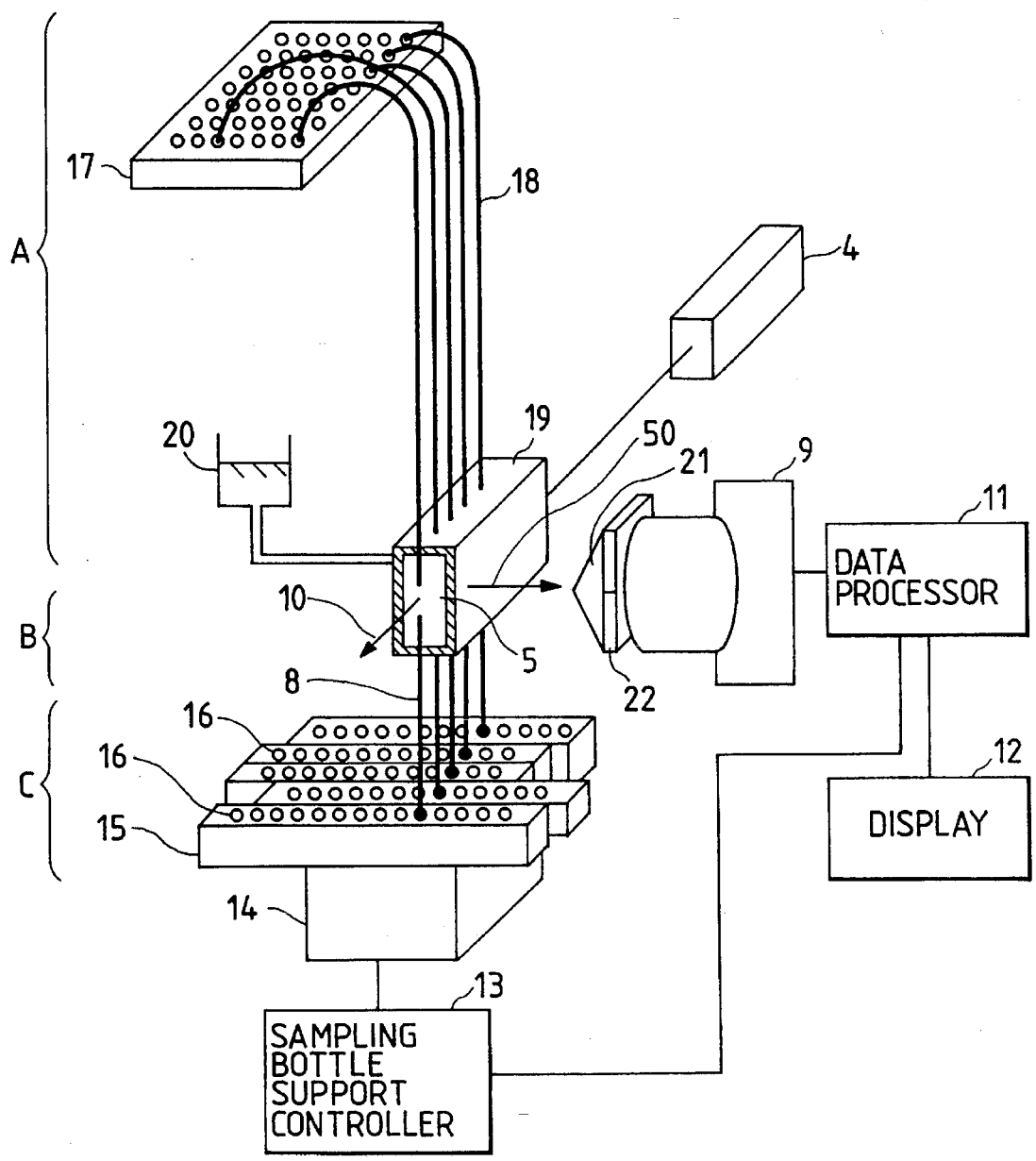
FIG. 2 is a perspective view showing the second embodiment of the fraction collector according to the present invention.

FIG. 2 shows the second embodiment of the present invention. The same symbols as those in FIG. 1 denote the same members or the sites having the same functions. This device is an application of the present invention to the electrophoresis device disclosed in the Specification on the invention related to Japanese Patent Laid-open NO. 6-138037. The separating medium A is composed of multiple capillary gel electrophoresis tube 18, similar to the case of the invention related to Japanese Patent Laid-open NO. 6-138037, and the collecting portion C has virtually the same as the first embodiment. The capillary tube having an outer diameter of 200 μm and inner diameter of 100 μm, for example, is used as gel electrophoresis tube 18 and sample transferring tube 8. Of course the bigger diameter of both capillary tubes can be used. Polyacrylamide having a concentration of 5 to 20 percent or agarose having a concentration of 0.5 to 3 percent is used as the gel to be loaded in the gel electrophoresis tube 18. Detecting portion B uses the excitation light from the light source of He-Ne laser (having a fluorescent wavelength of 594 nm). For example, the laser light is focused to about 100 μm in diameter at the focal position so that the laser light diameter will be about 100 μm over the region of about 10 mm on the front and rear of the focal point. Accordingly, if gel electrophoresis tubes 18 having an outer diameter of 200 μm and inner diameter of 100 μm are arranged at intervals of 400 μm, about 50 tubes can be laid out in the region of about 10 mm on the front and rear of the focal point. This makes it possible to irradiate close to the terminus of the gel electrophoresis tube 18 with the uniform light beam diameter and light intensity. The top ends of ample transferring tubes 8 are arranged in opposition to gel electrophoresis tubes 18. FIG. 2 gives a linear representation of the sample transferring tube 8 to illustrate a schematic view of the device. Actually, sample transferring tube 8 is bent at the mid-position to ensure that each bottom of the sample transferring tube 8 is located over the specified sampling bottle 16 of each sampling bottle support 15. Two-dimensional detector 9 uses the one disclosed in the Japanese Patent Laid-open NO. 2-269936. This detector is provided with the image splitting prism 21 having multiple optical planes to split the linear fluorescent image gained by irradiation of the excitation light, and multiple images split by the multiple planes of prism 21 are individually formed on the detection surface. Namely, after the signal light is split into two light paths by the use of image splitting prism 21, two different color filters 22 are used for selection and detection by wavelength.

Combination of the image splitting prism which allows splitting of the light into three or more light paths and the corresponding color filter allows selection and detection of light of more wavelengths. Buffer solution is supplied to the buffer vessel 5 from the container for sheath solution 20 positioned above the buffer vessel 5 also serving as fluorescent cell 19 by means of the gravity feed. It can also be be supplied by application of pressure to the buffer solution by such a means to supply pressure as the pump.

Multiple gel electrophoresis tubes 18 are arranged in a line between the upper electrode vessel (not illustrated) where the top end of the multiple gel electrophoresis tubes 18 immersed in buffer vessel 5. A great number of samples to be measured are put into multiple holes on sample holding plate 17, and the top end of each gel electrophoresis tube 18 is immersed in each of the holes to load samples in the electrophoresis tube 18. Then these top ends are moved to the upper electrode vessel (not illustrated). Separation of the samples to be measured is carried out by application of the direct current between the upper electrode vessel and buffer vessel 5. Multiple sample transferring tubes 8 in the collecting portion C are arranged in a line in conformity to the arrangement of gel electrophoresis tubes 18, and the top end (entrance) is connected to the bottom of said vessel to ensure that the specified opposing gaps can be maintained with respect to the gel electrophoresis tube 18 in the buffer vessel 5. This results in the buffer solution inside buffer vessel 5 transferring into the sample transferring tube 8. In this case, separated components eluted from the gel electrophoresis tube 18 are introduced into the desired fractionation tube 8.

It should be noted that the distance between gaps is preferred to be about 0.5 to 10 mm. Essentially, the gap distance is preferred to be shorter since electrophoresis of the samples separated by electrophoresis will be facilitated by reducing the gap distance. From the viewpoint of device assembling, however, adjustment will be more difficult if the gap is longer. Normally, it can be set to 10 mm or less in practice; the limit is determined by the scattering of the laser light at the capillary edges because the scattering should be avoided for a high sensitivity detection. It depends on the diameter of the excitation light such as laser light in gaps. Conversely, a longer distance of gaps will lead to easier diffusion of samples. It has been confirmed by the inventors that the gap distance of about 10 mm ensures smooth flow of the samples. Namely, gap distance of 0.5 mm to 10 mm allows easy and effective feed of the separated components from the gel electrophoresis tube 18 to the desired fractionation tube 8 in a selective manner.

Figure 3:
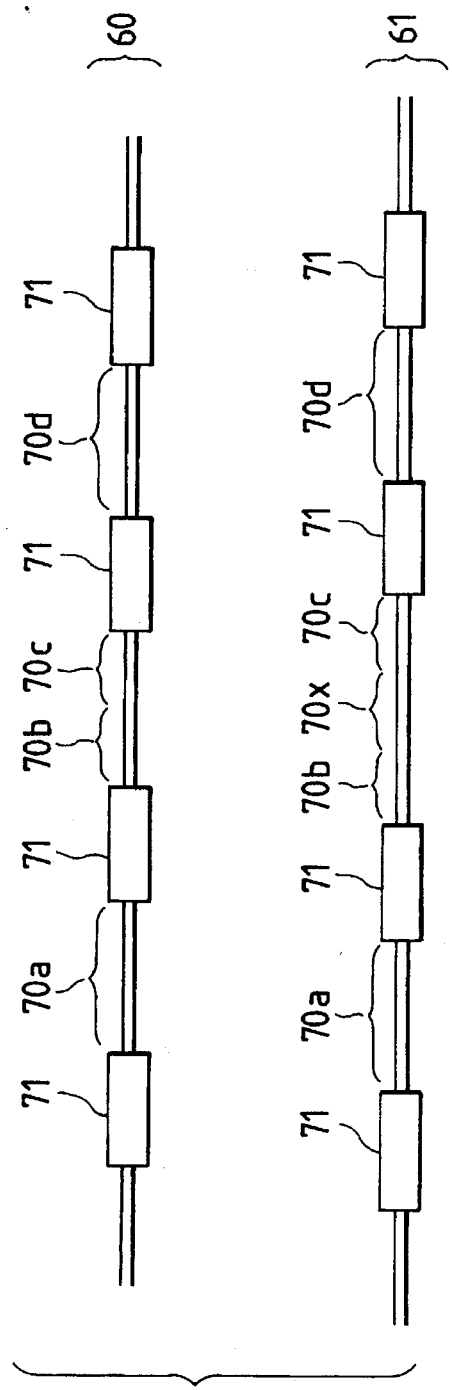
FIG. 3 is a drawing representing an example of the base sequence of part of DNA to be fractionated.

The present embodiment provides a device suited to fractionation of plural DNAs using the same gel electrophoresis tube 18 to separate the multiple samples labeled with fluorophore having different fluorescent wavelengths. The following describes the procedure for measuring the DNA:

FIG. 3 is parts of the schematic diagram of double stranded DNA structures having partially different DNA base sequences. In said Figure, 70 (70a to 70d, 70x) and 71 denote individual base sequence units. Base sequence unit 71 can be cut by the specific 6-base recognition enzyme ECoRI. DNA 60 on the top of the drawing does not have the base sequence unit 70X which is a part of the DNA 61 at the bottom of the drawing. Other portions are the same for both. For DNAs 60 and 61, the fluorophore labeled DNA fragments are obtained by connecting the DNA oligomer labeled with fluorophore in advance to the cutting site through ligation reaction after having been digested by the specific 6-base recognition enzyme ECoR.

Figure 4:
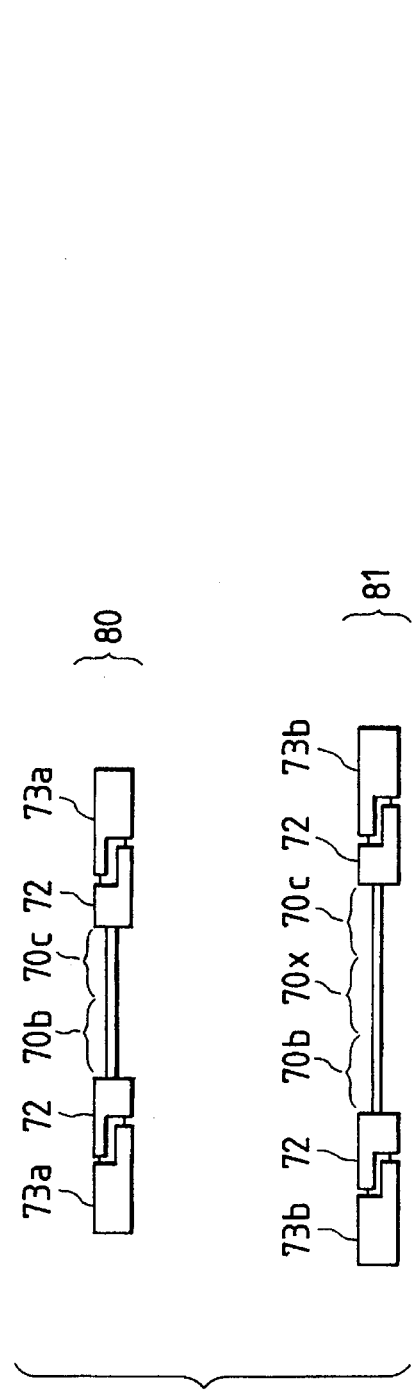
FIG. 4 is a drawing showing an example of the base sequence of the DNA fragment labeled with fluorophore.

In FIG. 4, the reference numerals 80 and 81 denote the fluorophore labeled DNA fragments which have been obtained by digesting DNAs 60 and 61, and which have different base sequences. DNA fragment 80 is labeled with fluorophore, using the DNA oligomer 73a which is labeled with sulforhodamine 101 (having a fluorescent wavelength of 620 nm), for example. On the other hand, the DNA fragment 81 is labeled with fluorophore, using the DNA oligomer 73b labeled with Cy-5 (having a fluorescent wavelength of 650 nm), for example. Two DNAs 60 and 61 are digested at base sequence unit 71 by 6-base recognition enzyme ECoR, and the cutting site 72 is connected with DNA oligomer 73a or DNA oligomer 73b. After mixing two DNA fragments 80 and 81 shown in FIG. 4 by adjusting the concentration so that the fluorescence intensity will be equal to each other, they were mixed with the buffer solution to prepare the sample to be measured.

Figure 5A:
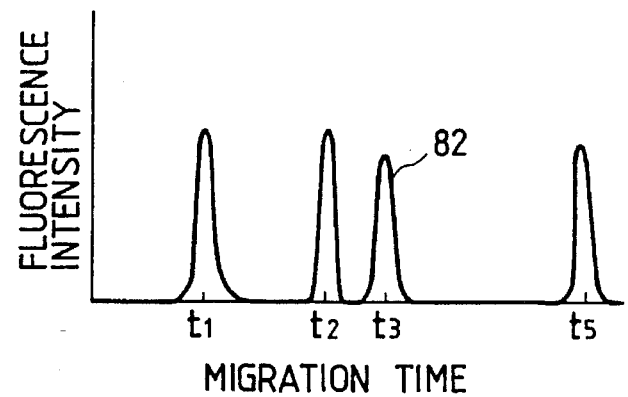
FIGS. 5A, 5B and 5C are drawings representing an example of the electropherogram obtained from the DNA fragment labeled with fluorophore.
Figure 5B:
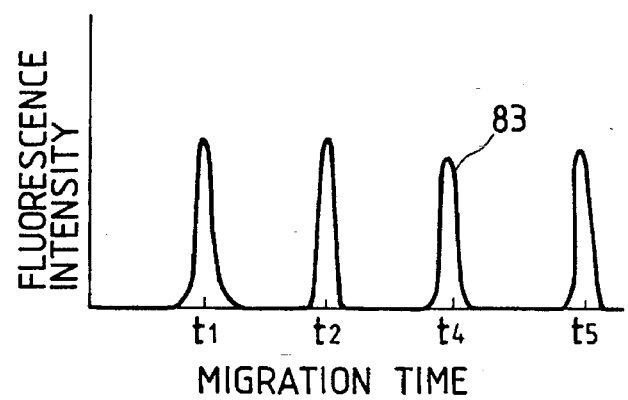

Samples prepared in this way are loaded into one of the gel electrophoresis tubes 18 for analysis, and are electrophoresed to be eluted into the buffer vessel 5. The two-dimensional detector 9 is used to detect fluorescence emitted from DNA fragments 80 and 81. FIGS. 5A and 5B show part of the electropherograms obtained by detecting fluorescence of a wavelength of 620 nm and 650 nm observed after start of the electrophoresis. The reference numeral 82 observed at migration time $t_3$ in FIG. 5A represents the fluorescence signal from DNA fragment 80, whereas the 83 observed at migration time $t_4$ in FIG. 5B represents the fluorescence signal from DNA fragment 81. What is observed at migration time $t_1$, $t_2$ and $t_5$ in FIGS. 5A and 5B shows the fluorescence signal from the DNA fragments which are obtained by cutting DNA 60 and DNA 61 and which have common base sequences.

Figure 5C:
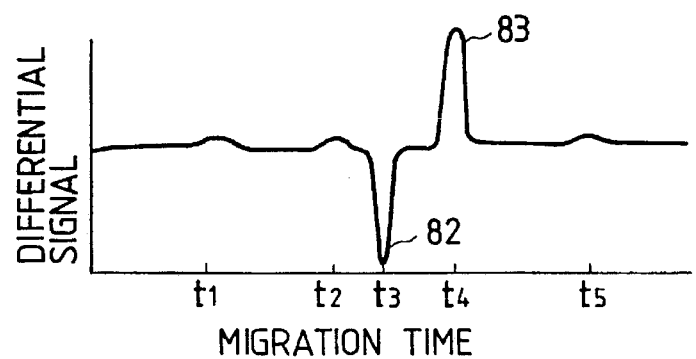

FIG. 5C depicts the differential spectrum obtained from two electropherograms shown in FIGS. 5A and 5B. The fluorescence signal at migration time $t_1$, $t_2$ and $t_5$ is shown as a trace in terms of the differential spectrum when the difference is found, while the fluorescence signal at migration time $t_3$ and $t_4$ is made distinct as differential spectrum. Accordingly, it can be seen from the differential spectrum in FIG. 5C that two DNA fragments 80 and 81 can be separated from each other and detected. Data processor 11 is used to carry out operational processing to obtain the differential spectrum. Based on the result of differential spectrum obtained by operational processing, the sampling bottle support controller 13 controls transfer device 14, and the transfer device 14 moves the sampling bottle support 15. The sampling bottle 16 is replaced by the specified sampling bottle 16 for collection, and two DNA fragments 81 and 81 are separated from each other, thereby being collected into different sampling bottles 16.

Use of the fraction collector according to the present invention permits saving of the time to obtain gel and fractionating the separated component by detecting the signal light emitted by the samples separated by the electrophoresis and by controlling the sampling bottle support. When fluorescence is used as fluorescence signal, the collector according to the present invention provides highly sensitive fractionation of a very small amount of samples. Furthermore, using the detector which is capable of detecting light of multiple wavelengths, it is possible to fractionate multiple samples by means of the same electrophoresis track. The present specification describes the case of fractionating the DNA fragments. The device according to the present invention can be used to fractionate such protein as RNA fragment and amino acid.

Figure 6:
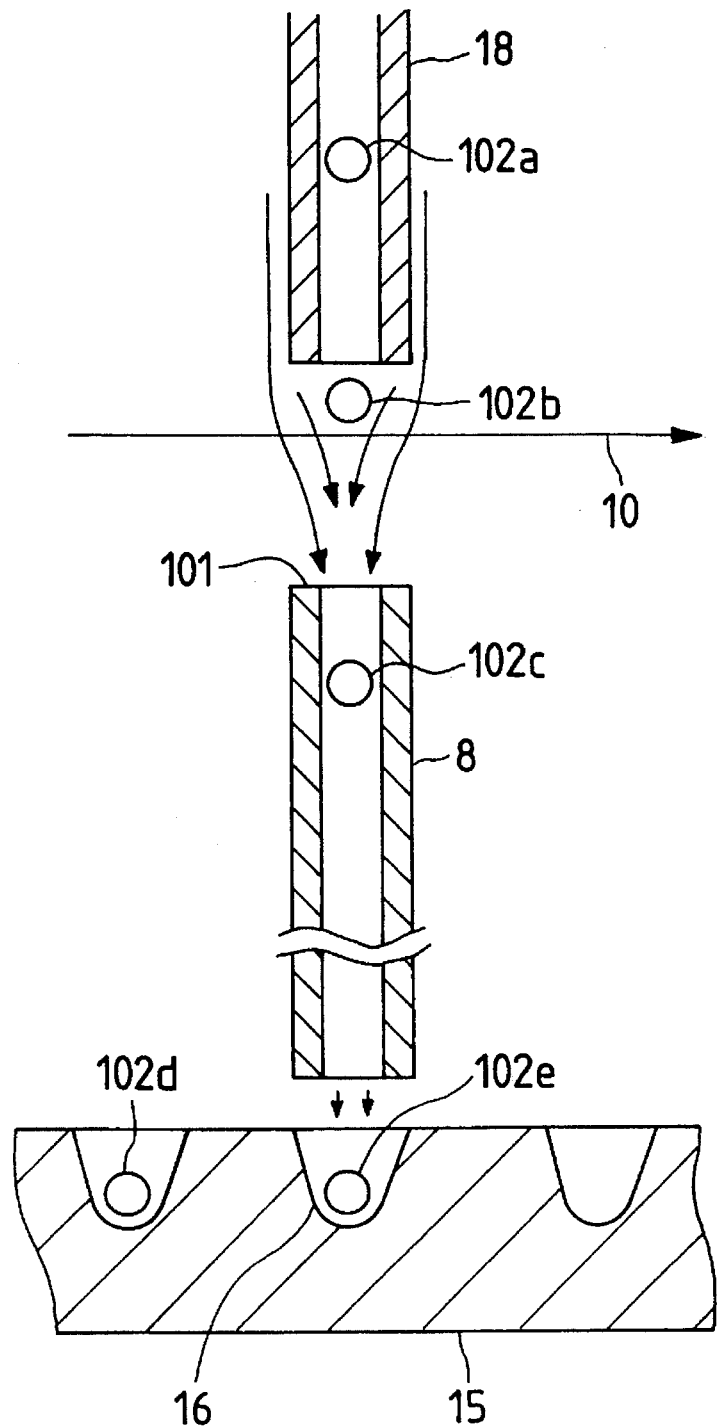
FIG. 6 is a schematic drawing showing the transfer of the sample by sheathflow.

The following gives approximate description of the sample transport by sheathflow, using the FIG. 6 and an example of the capillary gel electrophoresis tube. Enveloping capillary gel electrophoresis tube 18, the buffer solution flows down spontaneously toward the entrance 101 of the capillary sample transferring tube, and goes into the capillary sample transferring tube 8 (sheathflow). In FIG. 6, the flow of buffer solution is indicated by upper and lower arrow marks. The reference symbol 102a denotes the component separated by electrophoresis through the capillary gel transfer tube 18. The reference symbol 102b shows the separated component which is eluted from capillary gel electrophoresis tube 18 to flow in the gap between the capillary gel electrophoresis tube 18 and capillary sample transferring tube 8, being enveloped by the flow of buffer solution. The reference symbol 102c denotes the separated component flowing through the capillary sample transferring tube 8. Since the separated component 102b enveloped by buffer solution flows into the capillary sample transferring tube 8 facing the capillary gel electrophoresis tube 18, the separated components eluted from multiple electrophoresis tracks without being mixed with one another are fed to the sample transferring tubes facing the electrophoresis tracks. While flowing through the gap, separated components 102b are exposed to excitation light 10, and fluorescence is emitted from the fluorophore as the label of separated component 102b. This fluorescence is detected by means of the two-dimensional detector; then sampling bottle support 15 is moved, and the separated components flowing through the capillary sample transferring tube 8 are fractionated into the sampling bottles 16 on the sampling bottle support 15. The reference symbol 102e denotes the separated component fractionated, and 102d denotes the separated component fractionated preceding the separated component 102e.

What is claimed is:

1. A fraction collector comprising:
   a separating means composed of electrophoresis tracks to separate samples by electrophoresis,
   a transferring means to transfer separated components eluted from said electrophoresis tracks, said transferring means comprising capillary sample transferring tubes which are placed with their ends close to the ends of said electrophoresis tracks at a specified gap,
   a transport means to supply buffer solution to said gap and to carry said separated components into said sample transferring tube by sheathflow of said buffer solution,
   a fractionating means to fractionate said separated component having moved inside each of said sample transferring tube,
   a detecting means to detect elution of said separated component by detecting light emitted from said separated component at the gap, and
   a control means to control said fractionating means based on a signal gained by said detecting means.

2. A fraction collector according to claim 1 wherein said separating means comprises electrophoresis tracks formed on the electrophoresis plate using a slab gel.

3. A fraction collector according to claim 1 wherein said separating means comprises capillary gel electrophoresis tubes.

4. A fraction collector according to claim 1 wherein said samples are labeled with fluorophore, said gaps are provided with a light source to irradiate excitation light, and said detecting means is an optical detector to detect fluorescence emitted from said separated components in response to the excitation light.

5. A fraction collector according to claim 4 wherein said fractionating means includes sampling bottle supports which are movably placed with their ends close to the ends of said sample transferring tubes, said sampling bottle supports being provided with multiple sampling bottles, said control means comprises a sampling bottle support control means to control the transfer device to move sampling bottle supports, and said sampling bottle support control means controls said transfer device based on the signal output from said optical detector to fractionate the separated components into the specified sampling bottles.

6. A fraction collector according to claim 5 wherein said sampling bottle support control means controls said transfer device in a specified time after having detected the fluorescence based on the signal output from said optical detector.

7. A fraction collector according to claim 6 wherein said specified time is shorter than the time from when said separated components are exposed to the excitation light until they move to said sampling bottle supports by passing through said sample transferring tubes.

8. A fraction collector according to claim 6 wherein said specified time is shorter than the time from when the specified substances are electrophoresed in said electrophoresis tracks before separation and fractionation of said sample, until said substances move to said sampling bottle support from the site where said excitation light in said gaps is irradiated.

9. A fraction collector according to claim 1 wherein said gaps are arranged in a linear form.

10. A fraction collector according to claim 9 wherein said samples are labeled with fluorophore, and the light source to irradiate said gaps is further provided.

11. A fraction collector according to claim 5 wherein said samples are classified into multiple groups which are labeled with fluorophores which are different for each group and wherein said sampling bottle support control means controls said transfer device based on the difference of fluorescence intensities emitted by said different fluorophores detected by said optical detector.

12. A fraction collector according to claim 1 wherein the ends of said electrophoresis tracks and those of said sample transferring tubes are connected to the solution vessel where said buffer solution enters.

13. A fraction collector comprising:
   an electrophoresis means to separate fluorophore-labeled samples by electrophoresis,
   a light source to excite said fluorophore to cause fluorescence to be emitted,
   a light detecting means for detecting said fluorescence,
   a fractionating means to fractionate the samples separated by electrophoresis, and
   a control means to control said fractionating means, based on the detection signal gained from said optical detector.

14. A fraction collector according to claim 13 wherein said electrophoresis means is provided with electrophoresis tracks, and, furthermore, comprises;
   a transfer means which transfers separated components eluted from said electrophoresis tracks and which is composed of capillary sample transferring tubes with their ends placed close to the ends of said electrophoresis tracks at specified gaps, a transport means to supply the buffer solution to said gaps and to carry said separated component to said sample transferring tube by sheathflow of said buffer solution, and sampling bottle supports which are movably placed with other ends said sample transferring tubes, said sampling bottle supports being provided with multiple sampling bottle, and wherein said control means comprises a sampling bottle control means to control the transfer means to transfer the sampling bottle supports, and, said sampling bottle support control means controls the said transfer device based on the signal output from said optical detector, thereby fractionating said separated components and putting them into the specified sampling bottle.

15. A fraction collector comprising;

a separating means composed of a single electrophoresis track to separate samples by electrophoresis, a transfer means which transfers a separated component eluted from said electrophoresis track and which is composed of a single capillary sample transferring tube with its end placed close to the end of said electrophoresis track at a specified gap, a transport means to supply the buffer solution to said gap and to carry said separated component to said sample transferring tube by sheathflow of said buffer solution, a fractionating means to fractionate the separated components having moved inside said sample transfer tube, a detecting means to detect the elution of said separated component by detecting the light emitted from said separated component, and a control means to control said fractionating means based on a signal gained by said detecting means.

* * * * *